(12) United States Patent
Shanks et al.

(10) Patent No.: US 7,885,708 B2
(45) Date of Patent: Feb. 8, 2011

(54) IONTOPHORESIS DEVICE

(75) Inventors: Steven C Shanks, McKinney, TX (US); Kevin B Tucek, McKinney, TX (US)

(73) Assignee: Erchonia Corporation, McKinney, TX (US)

( * ) Notice: Subject to any disclaimer, the term of this patent is extended or adjusted under 35 U.S.C. 154(b) by 867 days.

(21) Appl. No.: 11/880,714

(22) Filed: Jul. 24, 2007

(65) Prior Publication Data
US 2008/0021372 A1  Jan. 24, 2008

Related U.S. Application Data

(63) Continuation-in-part of application No. 10/346,149, filed on Jan. 15, 2003, now Pat. No. 7,341,597.

(51) Int. Cl.
A61N 1/30 (2006.01)
A61H 33/00 (2006.01)

(52) U.S. Cl. .......................................... 604/20; 607/86
(58) Field of Classification Search .................. 604/20; 607/2–3, 85–86; 205/701, 742–761; 210/748.01, 210/748.16–748.18, 749, 764
See application file for complete search history.

(56) References Cited

U.S. PATENT DOCUMENTS

| 2,263,205 | A | * | 11/1941 | Conrad .................. 604/20 |
| 3,616,355 | A | | 10/1971 | Themy et al. |
| 3,752,747 | A | | 8/1973 | Treharne et al. |
| 4,291,125 | A | | 9/1981 | Greatbatch |
| 4,337,136 | A | | 6/1982 | Dahlgren |
| 4,492,618 | A | | 1/1985 | Eder |
| 4,654,071 | A | | 3/1987 | Muller |
| 4,850,956 | A | | 7/1989 | Bontemps |
| 4,915,685 | A | | 4/1990 | Petelenz |
| 5,282,940 | A | | 2/1994 | Griffis et al. |
| 5,603,843 | A | | 2/1997 | Snee |
| 5,741,317 | A | | 4/1998 | Ostrow |
| 6,009,345 | A | | 12/1999 | Hofmann |
| 6,482,309 | B1 | * | 11/2002 | Green et al. .................. 205/619 |
| 6,555,071 | B2 | | 4/2003 | Skrinjar |
| 6,597,947 | B1 | | 7/2003 | Inoue |
| 6,643,544 | B1 | | 11/2003 | Adachi |
| 6,970,739 | B1 | | 11/2005 | Inoue |

* cited by examiner

Primary Examiner—Mark W Bockelman
(74) Attorney, Agent, or Firm—Etherton Law Group, LLC; AnnMarie W. Whitley; Sandra L. Etherton

(57) ABSTRACT

A device for iontophoresis. A first battery-powered array is submerged into a liquid contained in a first reservoir and a second battery-powered array is submerged into a liquid contained in a second reservoir. Each array has one or more degradable electrodes that releases ions into the liquid in the reservoir. The electrodes can be copper, zinc, steel, nickel, or a combination thereof. At the first array one of the electrodes can be positively charged while at the second array one of the electrodes can be negatively charged. Alternatively, an electrode at the second array can be positively charged while an electrode at the first array is negatively charged. The solution in the reservoir may also contain positively or negatively charged ions. Powering the arrays causes the charged molecules contained in the liquid to transport through a patient's skin. The device uses a current and voltage regulator to deliver a regulated amount of current through the arrays regardless of the conductivity of the liquid, and electronic circuitry is used to control the duration, polarity, electrode choice, and intensity of the treatment. Excessive heat is dissipated with a heat sink.

6 Claims, 6 Drawing Sheets

IONTOPHORESIS DEVICE

CROSS-REFERENCE TO RELATED APPLICATIONS

This application is a continuation in part of U.S. application Ser. No. 10/346,149 now U.S. Pat. No. 7,341,597 filed Jan. 15, 2003.

FIELD OF INVENTION

This invention relates generally to iontophoresis and particularly to a device for non-invasively conducting a charged substance, such as a medication or bioactive-agent, transdermally.

BACKGROUND

Iontophoresis is a needle-free, non-invasive technology for delivering nutrients, medicines, vitamins, minerals, therapeutic agents, drugs or other bioactive agents through the skin using a small electric current. These beneficial bioactive agents are referred to herein generally as medicaments. In general, delivering such medicaments through iontophoresis involves applying an electromotive force that transports ions through the stratum corneum, the outermost layer of skin, and into the dermis, the inner layer of skin that is comprised of connective tissue, blood and lymph vessels, sweat glands, hair follicles and an elaborate sensory nerve network.

Iontophoresis has proven effective for many treatments. For example, iontophoresis can be used to drive pilocarpine across the skin barrier to stimulate sweating in the sweat chloride test for cystic fibrosis. Alternatively, iontophoresis can be reversed to draw a molecule such as glucose out through the skin, for example to measure blood glucose levels in diabetic patients. Ionotophoresis is also commonly used with anti-inflammatory medications and to treat many common illnesses, such as plantar fascitis, bursitis and hyperhidrosis. Iontophoresis can also be used to deliver genes, detoxify patients, reduce pain, or deliver nutrition into a patient's body. Examples of positively charged ions that can be driven into the skin by an iontophoresis device include zinc, copper, alkaloids, certain anesthetics, and certain vasodilating drugs. Examples of negatively charged ions that can be driven into the skin by an iontophoresis device include salicylate, fluoride, penicillin and insulin.

Compared to popular methods of delivering drugs, such as local skin patches, injections, or oral delivery, there are significant advantages to delivering medicaments through iontophoresis. First, compared to local skin patches, using iontophoresis enhances the skin's permeability, allowing for greater faster drug delivery, higher dose rates, and shorter treatment times. Second, compared to hypodermic injection, iontophoresis is non-invasive thereby increasing patient compliance, avoiding painful injections, and reducing the associated risk of infections. Finally, even compared to oral delivery of medications, iontophoresis has advantages. When medications are administered orally, they must pass through the digestive tract where absorption can vary significantly from individual to individual. Moreover, when taken orally, the drug must pass through the liver where it is not unusual for a significant amount of the drug to be inactivated. Iontophoretic delivery on the other hand allows a medicament to be absorbed in the circulatory system quickly, more reliably, and without patient discomfort or noncompliance.

Iontophoresis has historically been practiced by positioning two electrodes, an anode and a cathode, at some distance from each other on a patient and applying a low voltage between them for a long period of time. As a result, the charged atoms or molecules are transported actively by the force of the applied electrical field. Positively charged ions are driven into the skin at the anode while negatively charged ions are driven into the skin at the cathode. Regardless of the charge on the medicament, two electrodes are used in conjunction with the patient's skin to form a closed circuit that allows the flow of current between the electrodes. These traditional iontophoretic techniques have drawbacks. For example, one typical iontophoresis devices involve two electrodes, each with a patch or other surface for retaining a small amount of solution or gel containing a medicament. The electrodes and gel are placed on a patient's body at a distance apart, depending on where treatment is needed. Often a patient may feel discomfort or experience redness or burns where the electrode contacts the skin.

Another conventional iontophoresis device uses a reservoir for submerging a body part and the current is passed through the liquid in the reservoir. These devices suffer potential electrical shock hazard and severe overheating. Because standard AC current powers the devices during treatment, there is some risk that the patient would be shocked as a result of transient current spikes. The overheating is caused, in part, by high levels of salts or minerals in the water. These salts and minerals dissolve into their constituent ions, which increase the flow of current through the electrodes to an unsustainable level as the treatment proceeds. Elaborate fans and other moving parts have been devised to dissipate the heat.

Early devices also had no ability to choose from more than one electrode and no control over the duration, polarity or intensity of the treatment, other than to pull the plug from the power supply. Thus, a treatment was limited to one type of electrode and limited in duration and control. Additionally, the devices burned out frequently. The current and voltage spikes common to commercial AC power supplies exacerbated the burnout problem.

Therefore, it is an object of this invention to provide an iontophoresis device for with improved safety and convenience. It is also an object of this invention to provide a device for iontophoresis that reduces the potential electrical shock hazard and the potential for burns. It is another object to provide a device that does not overheat under normal operation. It is a further object to provide a device that has control over the duration, polarity and intensity of the treatment and allows the user to easily choose the most appropriate electrode for his purpose.

SUMMARY OF THE INVENTION

The present invention is a device for iontophoresis. A first battery-powered array is submerged into a liquid contained in a first reservoir and a second battery-powered array is submerged into a liquid contained in a second reservoir. Each array has one or more degradable electrodes that may release ions into the liquid in the reservoir. The electrodes are preferably copper, zinc, steel, nickel, or a combination thereof. At the first array one of the electrodes can be positively charged while at the second array one of the electrodes can be negatively charged. Alternatively, an electrode at the second array can be positively charged while an electrode at the first array is negatively charged. The solutions in the reservoirs may also contain positively or negatively charged medicament ions. Powering the arrays causes the charged molecules contained in the liquid to transport through a patient's skin. The device uses a current and voltage regulator to deliver a regulated amount of current through the arrays regardless of the conductivity of the liquid, and electronic circuitry is used to control the duration, polarity, electrode choice, and intensity of the treatment. Excessive heat is dissipated with a heat sink.

DETAILED DESCRIPTION OF THE INVENTION

Figure 1:
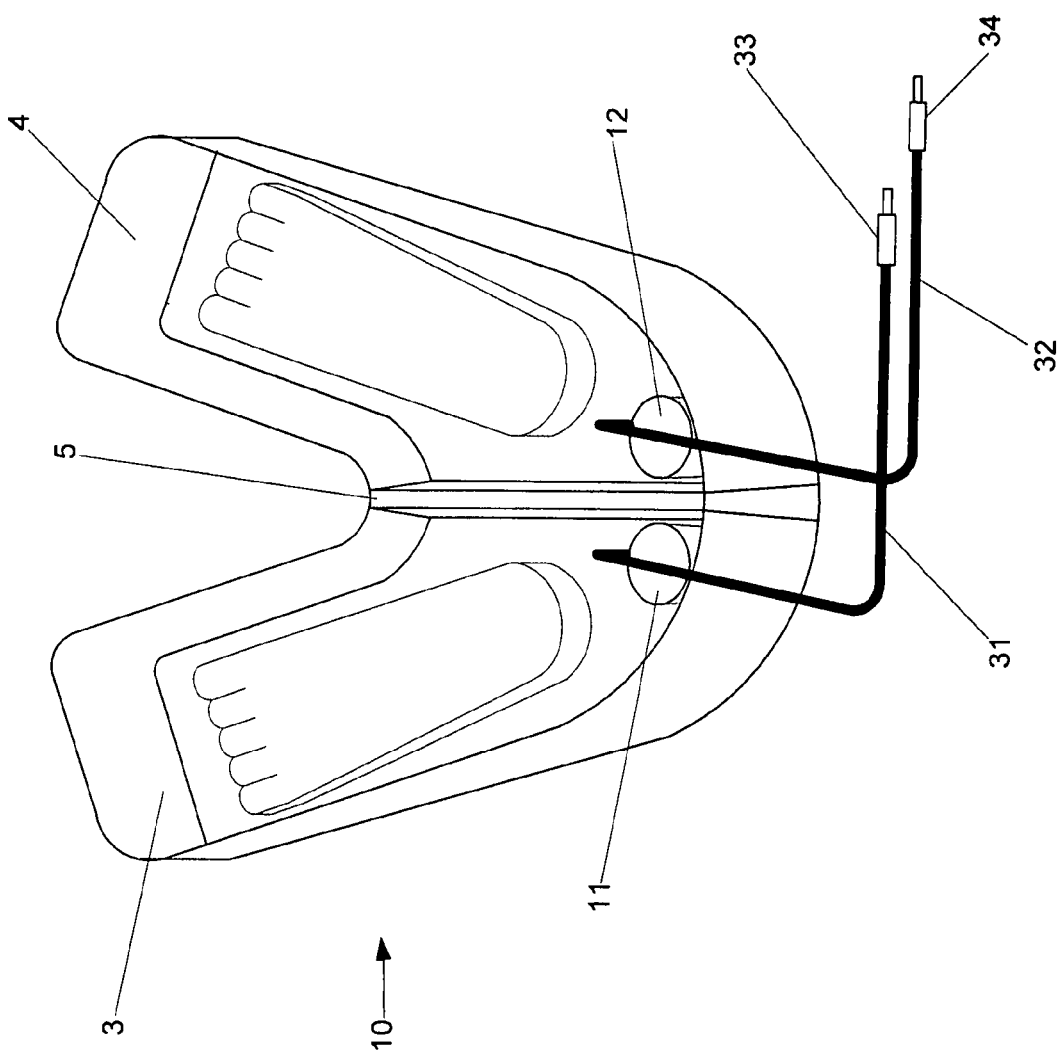
FIG. 1 is a perspective view of the iontophoresis device.

Referring to FIGS. 1-7, there is illustrated the preferred embodiment of the present invention, designated generally as device 10, which is used to perform iontophoresis. FIG. 1 illustrates device 10. Device 10 has a first reservoir 3 and a second reservoir 4 such that the liquid in reservoir 3 does not contact the liquid in reservoir 4. The reservoirs may be separate vessels or a single vessel separated by a partition 5. Also located in reservoir 3 and reservoir 4 are first and second arrays 11 and 12, respectively.

Figure 2:
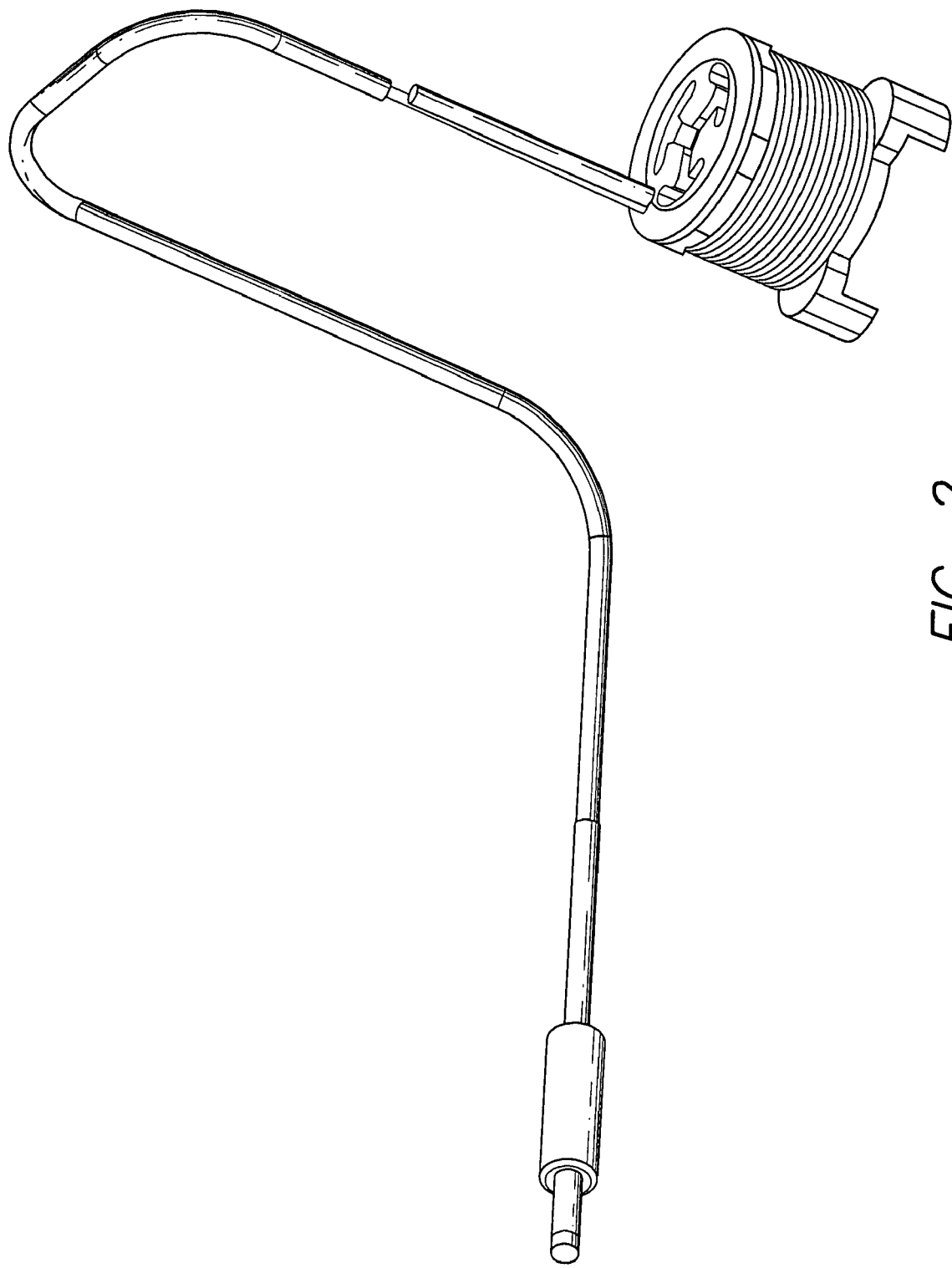
FIG. 2 is a perspective view of an array.
Figure 3:
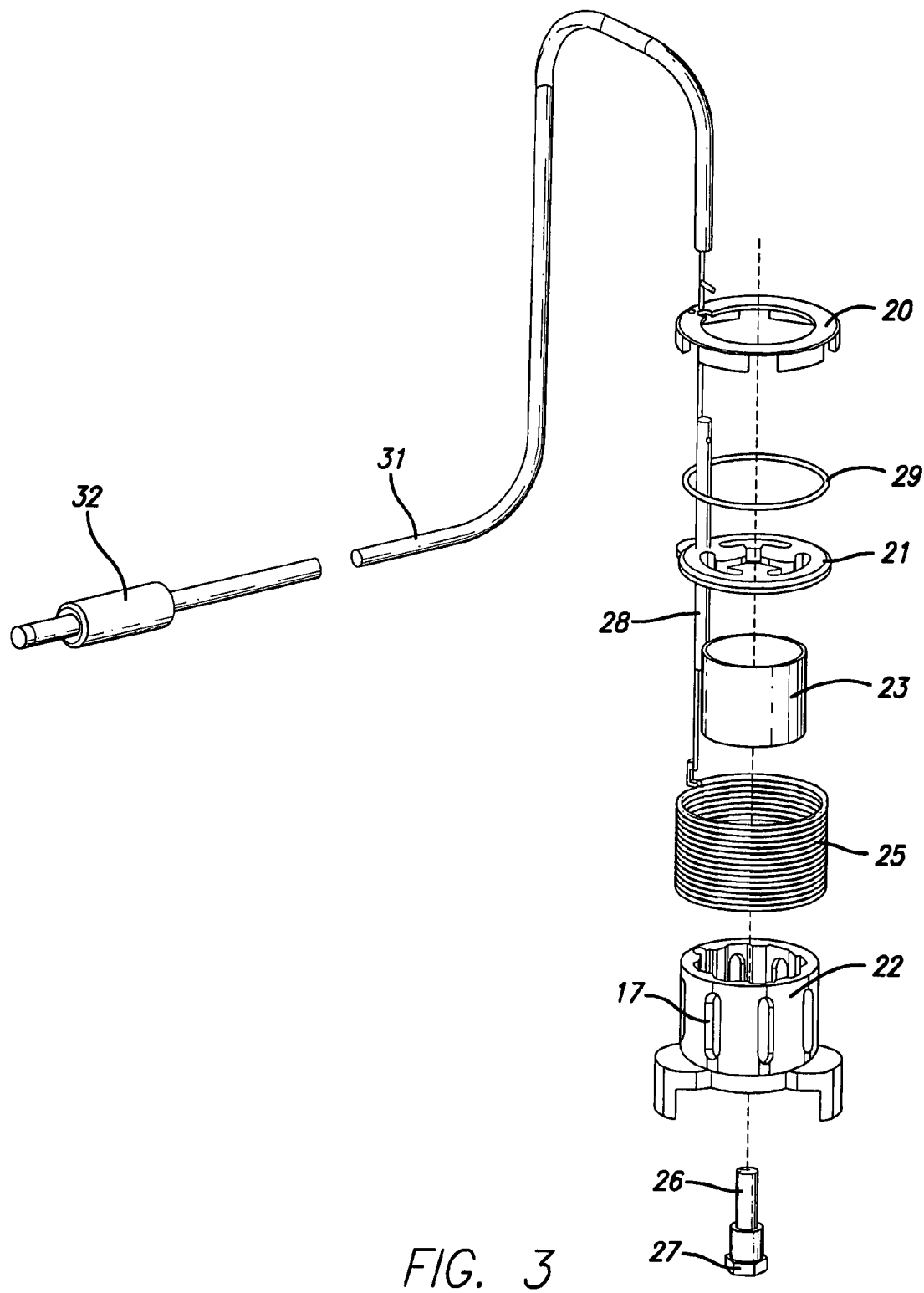
FIG. 3. is an exploded view of an array.
Figure 4:
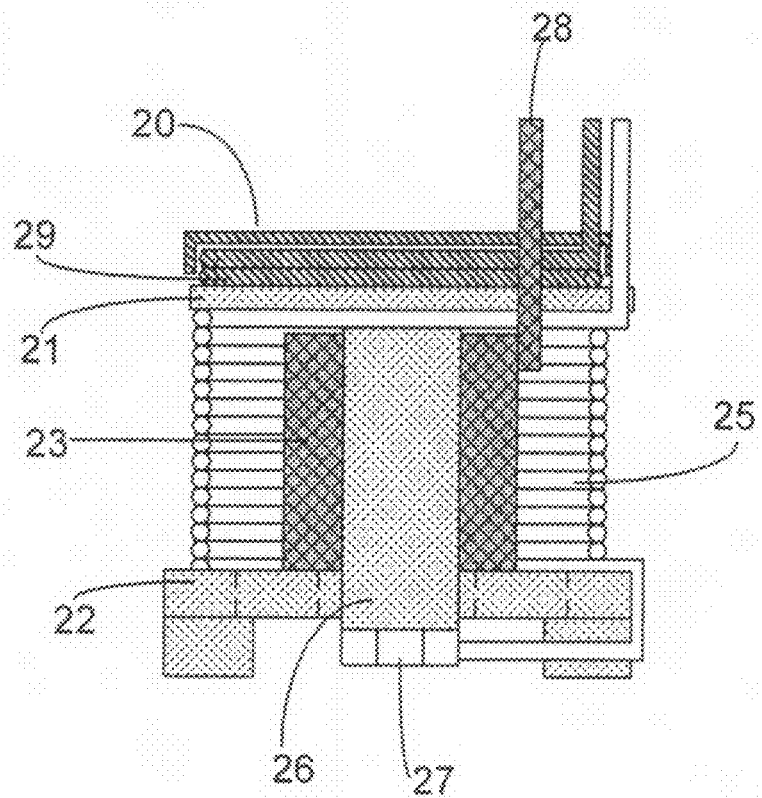
FIG. 4 is a cross-section of an array.

FIGS. 2, 3 and 4 illustrate first and second arrays 11 and 12, which are used to generate a current and drive ions contained in reservoirs 3 and 4 through the skin. Arrays 11 and 12 each have a cap 21 and a base 22 that form a housing to hold a first electrode 23 at a fixed distance from a second electrode. Cap 21 and base 22 have apertures in them through which the liquid can flow. The solution should be able to freely flow between the electrodes. Free horizontal flow is optimally achieved with side vents 17 on the base 22. Free vertical flow is optimally achieved by orienting the electrodes so that there is no vertical physical barrier. In the preferred embodiment, the electrodes are concentric rings in which the solution flows vertically in the spaces between the rings: this maximizes the amount of solution in contact with the electrodes and allows any bubbles to float freely to the surface.

Throughout this specification, the preferred materials are described for the electrodes. However, considering factors such as cost, availability, performance, and weight, other conductive materials, including metals, certain forms of carbon including graphite, and doped insulators will suffice. In each array, a first electrode 23 is connected to, or integral with, a rod 28, which is connected to a direct current source. The current source causes ions to be released from the array and thus transported through the skin. The ions alone may be transported through the skin, or the ions may bond with medicaments to be carried through the skin, or both. First electrode 23 is preferably a tubular assembly that sits inside of base 22. Preferably the first electrode 23 and rod 28 are stainless steel. Modern stainless steel usually contains iron, carbon, and chromium, and may also contain other elements, such as nickel, niobium, molybdenum, and titanium, all of which may be released from the array. The tubular assembly preferably has a circular cross-section such as that formed by a round tube of solid stainless steel or a stack of stainless steel washers, because a circular cross section has the advantage of uniform wear and uniform energy distribution. However, considering factors such as cost, ease of manufacturing, and performance such as the need to concentrate energy at a desired point, other shapes may be employed such as flat sheets, posts, spheres, or tubes of non-circular cross-section.

The second electrode has two components, a tubular first winding 25 and a core 26. The first winding 25 has a first end and a second end and is preferably made of copper. The first end of first winding 25 is connected to core 26 with a fitting 27, and the second end of first winding 25 is connected to a direct current source. First winding 25 surrounds, or winds around, base 22. First winding 25 is preferably a winding of copper wire, but the tubular shape may also be achieved with a copper tube. Preferably cap 21, first winding 25, first electrode 23, and base 22 are substantially concentric around core 26, as shown in FIG. 4. Core 26 is preferably made of zinc, and fitting 27 is preferably made of brass, an alloy of mainly copper and zinc.

FIGS. 2 and 3 further show that first array 11 also comprises a holder 20 and a second winding 29, both preferably made of nickel. Holder 20 holds second winding 29 atop or around cap 21 and substantially concentric around core 26. Second winding 29 is connected, preferably wired, to rod 28. Holder 20 is also connected to the direct current source. The second winding 29 is an optional third electrode.

Second array 12 preferably contains all of the elements present in first array 11, all of which made of the same materials as the elements in the first array. Alternatively, the second array may be made with different elements or of different materials. In some applications, it may be desirable to make one or more of the elements out of one or more metals that has a lower electronegativity than the others, so that the element degrades faster under applied current than others, in essence acting as a sacrificial anode. For example, using copper for the first winding 25 and zinc for the core 26, the core will degrade faster than the first winding because zinc has a lower electronegativity than copper.

Figure 5:
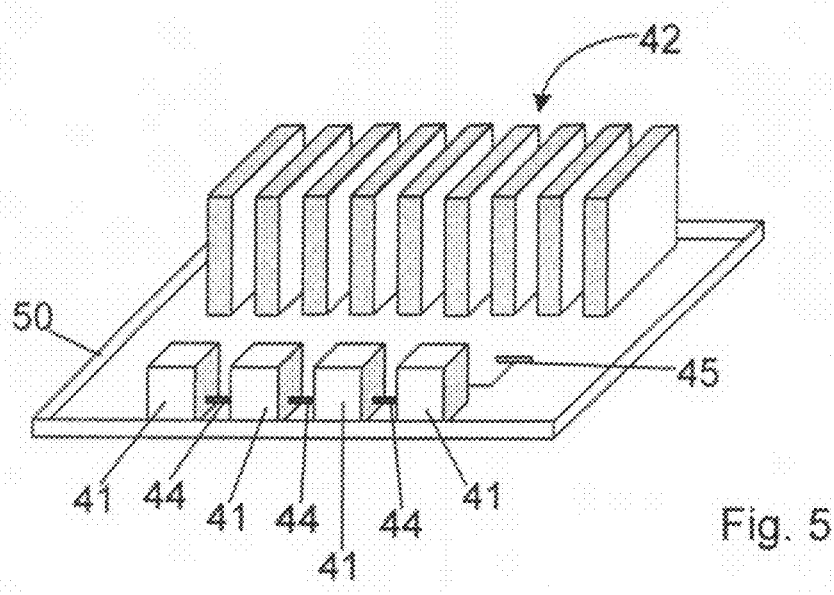
FIG. 5 illustrates the batteries and heat sink inside the control box.
Figure 6:
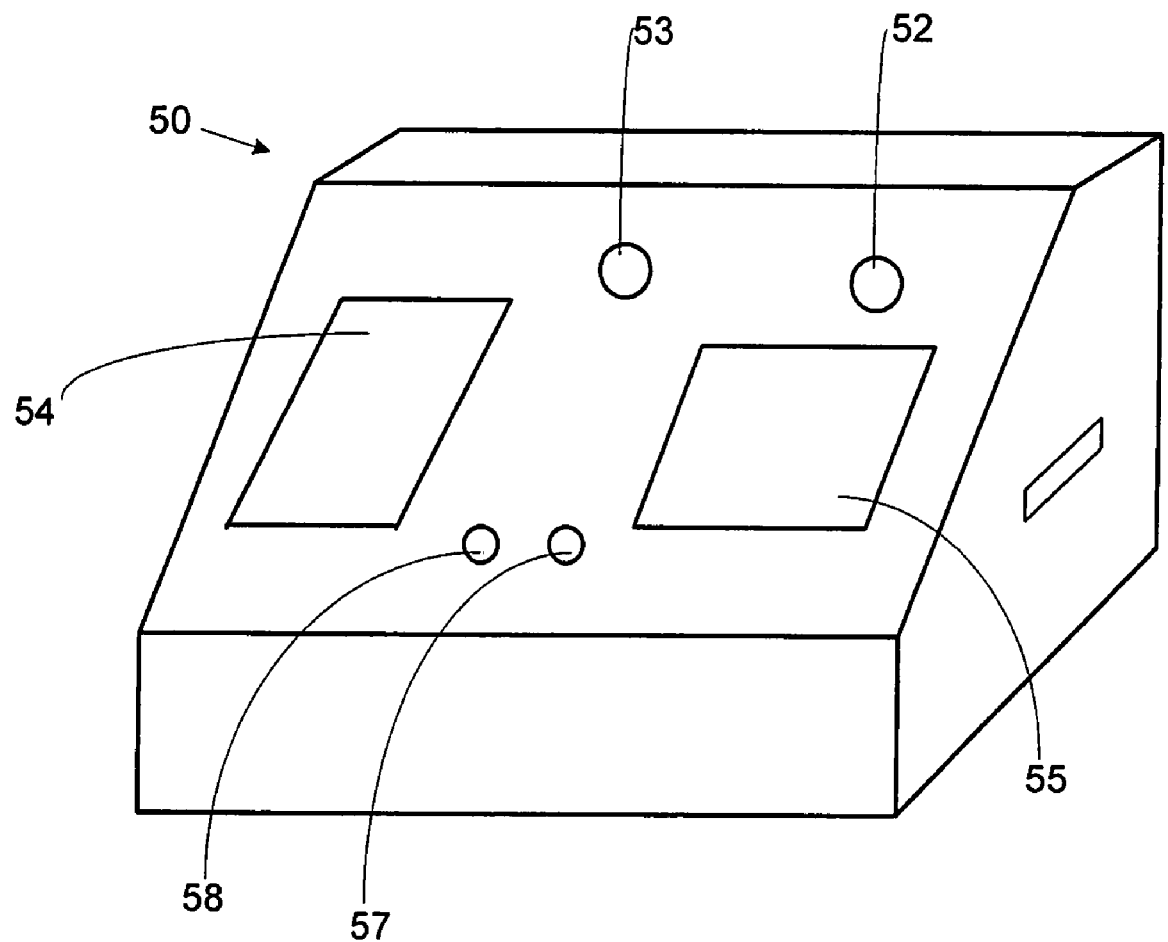
FIG. 6 is a front view of the control box.
Figure 7:
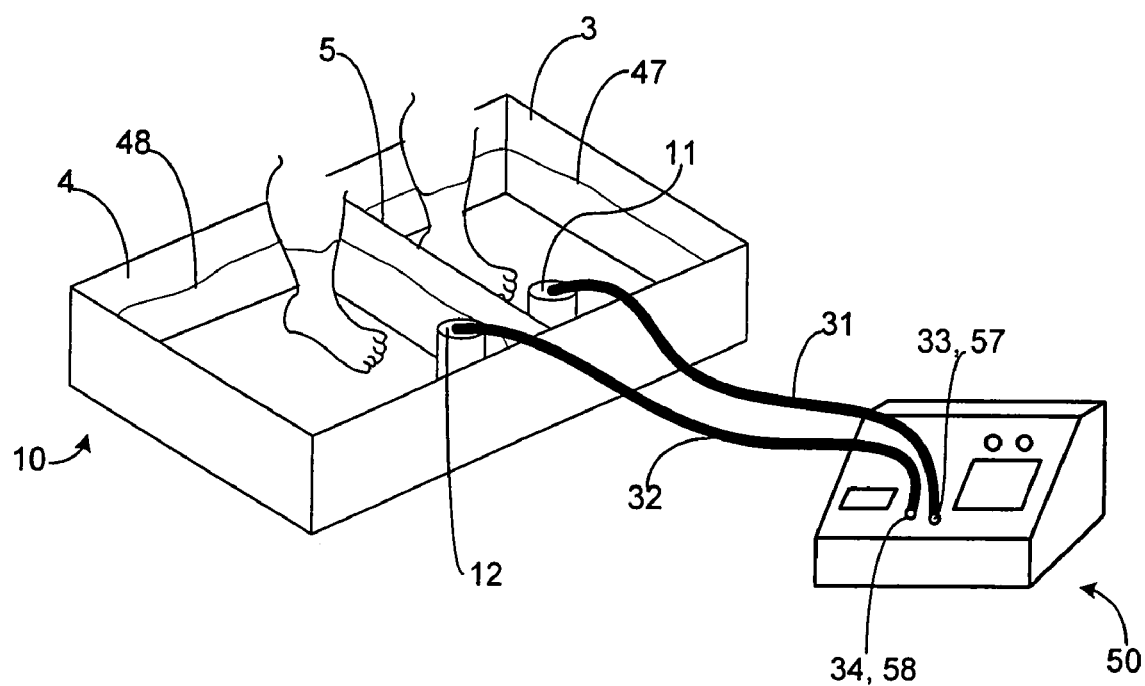
FIG. 7 illustrates a perspective view of the device in operation, with a patient's feet placed in separated reservoirs.

With respect to both first and second arrays 11 and 12, both have cords 31 and 32 and plugs 33 and 34 that connect them to a control box 50, as shown in FIGS. 5-7. Control box 50 houses the direct current source so that when arrays 11 and 12 are connected to control box 50, the direct current source is electrically connected to first array 11 and second array 12, preferably via a relay. A circuit is formed between the first array and the second array through the patient. The current may be pulsed for greater therapeutic benefit.

In addition to the direct current source, control box 50 also houses a heat sink 42, circuitry for regulating current and voltage to arrays 11 and 12, and circuitry for setting and controlling various parameters of the therapy. The direct current source preferably provides a maximum of 24V DC and draws less than 2 amps, which can be provided by battery or AC power supply converted to DC with the appropriate transformer. Preferably the direct current source is a set of four 6V rechargeable batteries, such as sealed lead acid batteries 41, Or, in another example, two 12V batteries could be used. FIG. 5 shows the batteries 41 seated in the bottom 40 of the control box 50, which are typically held in place with two large nylon or polypropylene battery holders (not shown). The batteries are connected in series with fuses 44 between adjacent cells, preferably 5 amp fuses. The fuses serve to prevent any inadvertent short-circuiting of the batter power source; a failure of the internal electronic circuitry or any internal wiring will blow a fuse, thereby preventing further power from being drawn from the batteries. Furthermore, any internal failure of the individual batteries themselves or failure of the insulating materials used within will also blow a fuse, thereby preventing any catastrophic damage to the device or the batteries themselves. The batteries can be recharged with standard AC current. Preferably, the control box 50 has a charge port 52 that is connected to AC current with an appropriate transformer or battery charger (not shown). The present device is not connected to AC power during use; instead, the device powered solely by direct current, preferably batteries.

A heat sink is housed in the control box 50 to dissipate any heat that may be generated. Preferably an aluminum heat sink 42 is used. The preferred heat sink 42 comprises a series of aluminum plates, spaced apart to allow airflow between the plates. Alternatively, a fan or water cooling system can be used to dissipate heat that is generated.

The control box 50 also houses circuitry to regulate power to at least arrays 11 and 12 and control the treatment parameters of the device. In an alternate embodiment, the control box can control multiple arrays so that multiple treatments can be given at the same time. Further, the circuitry provides the ability to store and recall several treatment protocols. Preferably the circuitry is digital, which is immune to drift or timing variations due to temperature changes and generates little heat. In the preferred embodiment, regulating circuitry regulates current and voltage to the array. This circuitry includes a current limiter 45 connected to the battery 41, which further serves to limit the maximum amount of current, regardless of the conductivity of the water.

The control box 50 circuitry controls the parameters of the treatment, including which electrodes in each array to charge, the duration, mode, intensity and pulse frequency. The parameter control circuitry includes an on/off switch that controls the delivery of power from the batteries 41 to the arrays 11 and 12; a timer for controlling the length of time the power is applied to the arrays; a switch for reversing to which array power is supplied and for selecting to which electrode the power is applied in each array; and a switch for varying the amount of power delivered to arrays 11 and 12. The circuitry may also include a rheostat or other potentiometer that enables the amount of applied current to be continuously or incrementally varied, depending on factors such as the body mass of the patient and type of medicaments. Additionally, the device may include a microcontroller and memory for storing pre-set programs. The present device allows positively or negatively charged molecules to be driven through a patent's skin in either first reservoir 3 or second reservoir 4. The parameters are changed by a patient, physician or other user via a user interface 54, preferably a keypad, accessible from the front of the control box 50. Information may be displayed on a display, preferably a liquid crystal display (LCD) 55, as is known in the art. The device also includes a master on/off key switch 53 and a charge port 52 for connecting the batteries to a source of power for recharging. As with the current limiter, the timers and switches are electrical components known in the art, as individual components or in integrated circuits.

In use, arrays 11 and 12 are submerged in a first liquid 47 and a second liquid 48 contained in reservoirs 3 and 4 respectively. The composition and number of the electrodes will depend on the treatment desired, as will the composition of the liquid and any medicament added thereto. First and second liquids 47 and 48 can be any type of solution or gel, as is known in the art. Preferably the liquid is water in both vessels, but each of the liquids may be different. One or both of the liquids may contain a medicament or other positively or negatively charged particles. Each of reservoirs 3 and 4 are large enough to accommodate the desired parts of a patient's body, such as a patient's hands or feet. The reservoirs are preferably made of a substantially electrically non-conducting material such as plastic or doped ceramic. The reservoirs may be thermally conductive, and may act to dissipate heat.

FIG. 7 illustrates the preferred embodiment in which a patient's feet 41 are submerged in liquid filled reservoirs 3 and 4. The liquid in first reservoir 3 contains a positively charged medicament medicine. First array 11 attaches to control box 50 by inserting male plug 33 into a female port 57 to access the direct current source. Similarly, second array 12 attaches to control box 50 by inserting male plug 34 into a female port 58 to access the direct current source.

In one embodiment of the present invention, after the device is turned on and the treatment protocol selected, first array 11 is positively charged and second array 12 is negatively charged. As a result, the charged particles contained in the liquid in first reservoir 3 from the medicament and the ions degraded from the array are transported through the patient's skin. Alternatively, if positively charged particles need to be transdermally delivered to the foot in second reservoir 4, the medicament is added to reservoir 4 and the polarity of treatment may be reversed, by switching the direct current source from first array 11 to second array 12, thereby changing the polarity of the arrays. If negatively charged particles need to be transdermally delivered at reservoir 3, the appropriate medicament is added to reservoir 3, and first array 11 is negatively charged while second array 12 is positively charge. Likewise, if negatively charged particles need to be transdermally delivered at second reservoir 4, the appropriate medicament is added to reservoir 4, and second array 12 is negatively charged while first array 11 is positively charged.

Further, with respect to each array, which electrode is positively or negatively charged can be selected as well by a patient, physician or other user through user interface 54. For example, if a particular medicine responds better when a copper electrode is charged, the copper electrode can be selected. Alternatively, if a particular medicine responds better when a nickel electrode is charged, the nickel electrode can be selected. Any of the first, second or third electrodes can be selected for charging. Alternatively, two of the electrodes can be charged, and not the third, or all of the electrodes can be charged at the same time. This allows a user to choose the best delivery method for a given medicine without having to substitute different arrays While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention not be limited to the particular embodiment disclosed, but that the invention will include all embodiments falling within the scope of the appended claims.

We claim:

1. An iontophoresis device comprising:
  a) a first and second array, each comprising:
    i. a cap having one or more apertures;
    ii. a copper winding having a diameter;
    iii. tubular stainless steel having a smaller diameter than that of the copper winding; the steel connected to the copper winding;
    iv. a zinc post having a smaller diameter than the steel tube, the zinc post connected to the copper winding;
    v. a base having one or more apertures;
    vi. a second winding having a diameter equal to or larger than the copper winding;
  wherein the cap, the second winding, the copper winding, steel, and base are substantially concentric around the zinc post;
  b) one or more rechargeable batteries connected between the first array and the second array, each of the batteries connected to each other in series with fuses between adjacent batteries;

c) a first reservoir for containing a first liquid, into which the first array is substantially submerged;
d) a second reservoir for containing a second liquid, into which the second array is substantially submerged;
e) a control box connected to the first and second arrays, the control box further comprising an
   i. an on/off switch;
   ii. a user interface for selecting parameters of the therapy;
   iii. a display for viewing the parameters;
   iv. a current limiter;
   v. a heat sink; and
   vi. a charge port for enabling the rechargeable batteries to be connected to a source of power;
such that when the on/off switch is turned on, the batteries supply direct current to at least one of the electrodes in the first array and charged particles in the first liquid are repelled by like charges from at least one of the charged electrodes and driven through the skin of a patient who has submerged a body part in the first reservoir.

2. The device according to claim 1 wherein the copper winding is connected to the zinc post with a brass fitting.

3. The device according to claim 1 wherein the first liquid contains a positively charged medicament and wherein the direct current source is applied to one of the electrodes of the array submerged in the positively charged medicament so that positively charged ions are driven through the skin of the body part submerged in the positively charged medicament.

4. The device according to claim 1 wherein the first liquid contains a negatively charged medicament and wherein the direct current source is applied to one of the electrodes of the array submerged in the negatively charged medicament so that negatively charged ions are driven through the skin of the body part submerged in the negatively charged medicament.

5. The device according to claim 1 wherein the second winding comprises nickel.

6. The device according to claim 1 wherein the second winding comprises stainless steel.

* * * * *